United States Patent [19]

Nuxhall et al.

[11] 4,020,676

[45] May 3, 1977

[54] METHOD AND APPARATUS FOR COLLECTING FLUID CONTAMINANTS

[75] Inventors: Orville Gene Nuxhall; Donald Thomas Carlton, both of Fort Wayne, Ind.

[73] Assignee: The Magnavox Company, Fort Wayne, Ind.

[22] Filed: Oct. 2, 1975

[21] Appl. No.: 619,082

[52] U.S. Cl. .............................. 73/61 R; 210/196
[51] Int. Cl.² ...................................... G01N 15/04
[58] Field of Search ............ 73/61.4, 61.1 R, 61 R, 73/53; 210/196, 387, 406, 416 R

[56] References Cited

UNITED STATES PATENTS

| | | | |
|---|---|---|---|
| 2,679,158 | 5/1954 | Claydon et al. | 73/61 R |
| 2,724,508 | 11/1955 | Luther | 210/416 R X |
| 2,734,377 | 2/1956 | Traver | 73/61.1 R |
| 3,138,015 | 6/1964 | Avery | 73/61 R |
| 3,251,469 | 5/1966 | Müller | 210/416 R X |
| 3,308,649 | 3/1967 | Colechia | 73/61 R |
| 3,782,175 | 1/1974 | Roman | 73/61 R |

Primary Examiner—Richard C. Queisser
Assistant Examiner—Joseph W. Roskos
Attorney, Agent, or Firm—T. A. Briody; Joe E. Barbee

[57] ABSTRACT

An apparatus to collect contaminants from a known volume of fluid and to present the collected contaminants for analysis. The apparatus has a first container to receive the known volume of fluid and a second container to receive the fluid from the container. A contaminant trapping material is located between the two containers so that as the fluid passes from the first container to the second container it passes through the contaminant trapping material. The second container is connected to a vacuum generator used to create a vacuum in the second container. The apparatus also has means to recirculate the fluid from the second container back to the first container so that the fluid can pass through the contaminant trapping material a given number of times thereby insuring an adequate collection of contaminants. A method of collecting contaminants from a fluid and presenting the contaminants for analysis is also disclosed.

4 Claims, 7 Drawing Figures

METHOD AND APPARATUS FOR COLLECTING FLUID CONTAMINANTS

BACKGROUND OF THE INVENTION

The present invention relates generally to apparatus and method for collecting and presenting contaminants from a fluid. More particularly, the present invention relates to collection and concentration of dissolved heavy metal ions in a fluid for the purpose of making analytical determinations.

With the increased concern for environmental pollutants, attention has been directed to detection and analysis of contaminants in fluids. Many forms of analysis have evolved including microscopic, chemical, and X-ray analysis.

In some cases, simple gravity was used to pass the fluid through a filter which was placed over the opening of a container and then particles trapped by the filter were analyzed. In others which attempted to speed up the flow of contaminated water through a filter, apparatus was designed that forced the water through the filter by increasing pressure on the water above the filter. And yet, other devices use a combination of increased pressure above and partial vacuum below the filter in order to pass the liquids through the filters. These devices were rather cumbersome to operate and required many gauges and valves to control the pressures. A feature missing from these prior art devices was the ability to recirculate the water through the filter in order to thoroughly collect the contaminants to perform an accurate analysis.

Of course, in the manual set-up wherein the filter was placed over the opening of the container and the liquid poured through the filter, the container had to be re-emptied and the liquid poured through the filter repeatedly to achieve the proper collection of contaminants. The inability of the prior art devices to permit multiple thru puts of the liquid through the filter does not allow the prior art devices to have the sensitivity of an apparatus that allows multiple thru puts. An apparatus that provides for multiple thru puts has the ability to concentrate the contaminants present in the liquid thereby improving the sensitivity of the collection apparatus and providing greater repeatability and reproducibility of the analytical results obtained.

A general shortcoming of prior art devices is their inability to collect dissolved constituents within a fluid. Most of the prior devices were intended to collect suspended particles.

In view of the foregoing, it should now be understood that it would be desirable to provide an improved fluid contaminant collection apparatus that would solve the above and other problems.

Accordingly, one of the objects of the present invention is to provide a fluid contaminant collection apparatus wherein multiple thru puts of the contaminated fluid is provided for.

Another object of the invention is to provide a fluid contaminant collection and presentation apparatus that allows the collection of dissolved constituents from a known volume of fluid.

Yet another object of the present invention is to provide an improved apparatus to collect and present a concentrated sample of contaminants from a known volume of fluid and to present the concentrated sample for X-ray analysis.

SUMMARY OF THE INVENTION

In carrying out the above and other objects of the invention in one form, we provide an improved apparatus to collect and present contaminants from a known volume of fluid. One embodiment of the invention has a first container to receive a known volume of fluid, a contaminant trapping material, and a second container. A reversible drive means to move the first container and the second container together thereby fixedly holding the contaminant trapping material in between the two containers. A vacuum generator means is used to create a vacuum in the second container. And means to recirculate the fluid from the second container back to the first container to allow the fluid to pass through the contaminant trapping material a predetermined number of times to extract additional contaminants.

A method of collecting and presenting a sample of contaminants from a known volume of fluid is also disclosed. The method comprises measuring a sample of fluid. Then placing a contaminant trapping material between a first and second container and bringing the first and second containers together thereby fixedly holding the contaminant trapping material between the two containers. The sample of fluid is emptied into the first container and a vacuum is generated in the second container so that the fluid will flow from the first container to the second container through the contaminant trapping material. Then the fluid is recirculated from the second container back to the first container so that the sample of fluid will pass through the contaminant trapping material again. The portion of contaminant trapping material containing the collected sample is then separated from the remainder of the material, which allows the collected sample to be presented for analysis.

The subject matter which we regard as our invention is set forth in the appended claims. The invention itself, however, together with further objects and advantages thereof, may be better understood by referring to the following detailed description taken in conjunction with the accompanying drawings.

Figure 1:
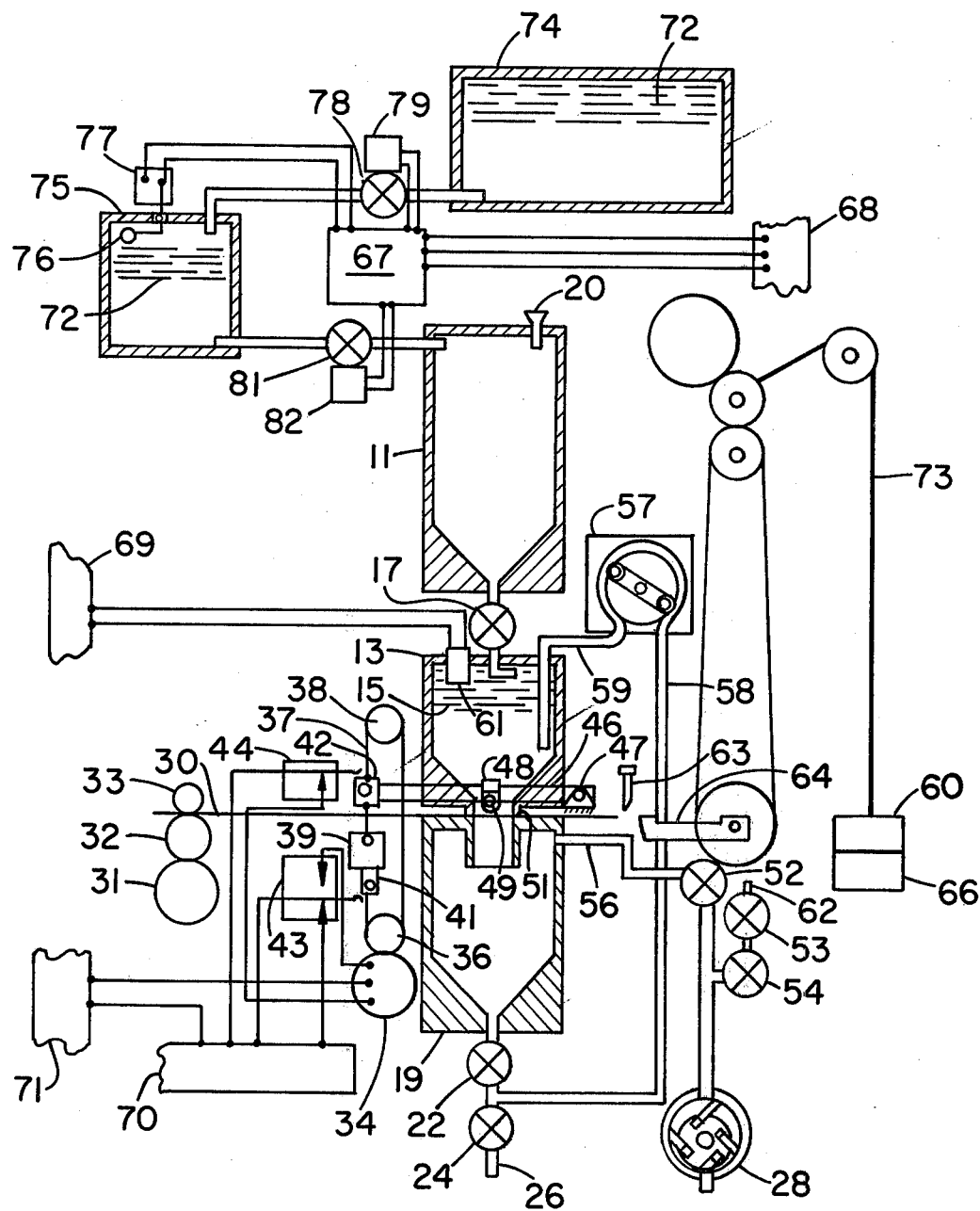
FIG. 1 is a schematic illustration of the overall apparatus embodying the invention in one form.

The exemplifications set out herein illustrate the preferred embodiments of the invention in one form thereof, and such exemplifications are not to be construed as limiting in any manner.

DESCRIPTION OF THE PREFERRED EMBODIMENTS

Before going into the detailed operation of components of the apparatus, a general functional description will be given. The contaminated fluid to be analyzed is premeasured and placed through fluid opening 20 into container 11. A filter or contaminant trapping material 30 is placed between containers 13 and 19 and containers 13 and 19 are then brought into close relationship thereby clamping filter trapping material 30. Valve 17 is then opened to allow the contaminated fluid to pass into container 13. Once the contaminated fluid is in container 13, vacuum pump 28 can be energized to draw a partial vacuum in container 19. The partial vacuum in container 19 assists the contaminated fluid in passing through the filter and into container 19. Once the contaminated fluid is in container 19, it can then be exhausted through drain port 26 or else it can be recirculated by energizing recirculating pump 57 so that additional contaminants can be removed by the contaminant trapping material 30. Once the contaminated fluid has been cycled through the contaminant trapping material 30 a sufficient number of times, it can be drained through drain port 26. Flushing solution 72 is used to flush the system once a contaminated fluid has been sampled and drained from the system. A programmer and controller is provided to achieve automatic or self-sequencing operation of the collection, presentation and analysis of the fluid sample.

The contaminant trapping material can be chelating resin or ion exchange material or any other suitable material that will collect dissolved constituents. However, it will also be appreciated that conventional filter material can be used to collect floating or suspended particles. We have found that a suitable filter material for collecting dissolved constituents is a cat-ion resin impregnated paper sold by Reeve-Angel Company of Cliffton, N.J.

Now referring particularly to FIG. 1, a reversible motor 31 is used to power drive roller 32 which advances and retracts the filter or contaminant trapping material 30. Idler roller 33 presses the filter against drive roller 32 so that motion is imparted to filter 30 as drive roller 32 rotates. A second reversible motor 34 is used to power drive sprocket 36 in a predetermined direction thereby causing chain 37 to move in a corresponding direction over sprocket 38. One end of chain 37 is connected to adapter link 42 which is connected to the draw bar spring nest while the other end is connected to draw bar piston 41. Draw bar piston 41 cooperates with draw bar spring nest 39 to pull adapter link 42 in a downward direction when drive sprocket 36 is rotated in a counter clockwise direction, conversely, adapter link 42 is pulled upward when drive sprocket 36 is rotated in a clockwise direction. Adapter link 42 is attached to lever 46 which rests on pin 49 and is pivoted at one end by a pin 47 so that when the adapter link 42 pulls the unpivoted end of lever 46 down the lever causes container 13 to move down to make contact with container 19 by the action of the lever resting on pin 49. An L-shaped clamp 48 is placed over lever 46 and also has a hole to permit pin 49 to fit through clamp 48, and accordingly, when one end of lever 46 is lifted container 13 is also lifted.

Switch assembly 43 is provided to sense when containers 13 and 19 are in proper position to securely hold or clamp contaminant trapping material 30 in place. Reversible motor 34 draws container 13 against the filter 30 and clamps the filter against the bottom of container 13 and the inlet of container 19. This is accomplished by turning drive sprocket 36 in a counter clockwise direction thereby drawing draw bar assembly 39 and piston 41 downward which in turn moves adapter link 42 downward simultaneously pulling that end of lever 46 downward. Lever 46 is pivoted on the opposite end by pin 47 and rests over pin 49 which is embedded into a ring at the bottom of container 13. An L-shaped clamp is positioned over lever 46 and has a hole which fits over pin 49. Draw bar piston 41 actuates switch assembly 43 thereby de-energizing motor 34 when the desired sealing or clamping force has been achieved. Preferably, motor 34 is equipped with an electromagnetic brake (shown in FIG. 4) to hold the clamping force on the contaminant trapping material when containers 13 and 19 are brought together.

Actuation of switch assembly 43 also signals controller 67 to energize the actuator of control valve 17 opening it and permitting a quantitative sample of contaminated fluid to enter container 13 from container 11. At this time the controller also starts a vacuum pump motor 28 and opens valves 54 and 52 by energizing their associated actuating devices. By closing recirculating valve 22 and opening vacuum valve 52 and energizing vacuum motor 28 a partial vacuum is created in container 19 which assists flow of contaminated fluid 15 through filter 30.

Vacuum adjust valve 53 is preset to a given value thereby permitting a predetermined vacuum to exist in container 19. Vacuum adjust valve 53 is intended to be preset prior to commencement of sampling a fluid. By adjusting vacuum adjust valve 53 and controlling the amount of vacuum in container 19, the flow rate of the contaminated fluid through filter 30 can be controlled. The higher the vacuum in container 19, the faster the contaminated fluid will flow through filter 30. However, in some cases, it is desirable to have the contaminated fluid flow at a slower rate through the filter thereby gathering a greater number of contaminants. This is particularly the case when collecting dissolved constituents from a fluid because slowing down the flow rate through the filter permits greater removal of dissolved elements in the fluid. Vacuum adjust valve 53 functions as a vacuum control valve by bleeding air into the vacuum pump thereby reducing the vacuum that is drawn into container 19.

An emitter-detector reflective optical sensor 61 is mounted in the cover of container 13. The presence of water in container 13 is detected by the optical sensor in the following manner. The sensor emits a beam of light which is aimed at the filter. The water surface, when present, reflects the emitted beam which is then detected by a light sensitive semiconductor in the sensor assembly. The appearance or disappearance of water above the filter within container 13 causes a change in the sensor output signal which will cause valves 52 and 54 to open with the appearance and close with the disappearance of water. Preferably, optical sensor 61 is located in the top of container 13 so that it is directly above the filter and therefore more effective in determining the presence or absence of fluid. With the disappearance of water in container 13 recirculating valve 22 is activated opening the valve and the recirculating motor pump 57 is energized thereby causing the contaminated fluid from container 19 to be recirculated back into container 13 through pipe 58 into pump 57 and then pipe 59.

When the apparatus is being used for dissolved ion filtration multiple exposures of the premeasured contaminated fluid to the filter may be required in order to achieve usable and desirable retention amounts of contaminants in the filter. Therefore, the number of cycles that the contaminated fluid will be cycled through the filter and the rate in which the contaminated fluid is set to flow through the filter depends upon which ions one is attempting to collect. Weaker ions require more exposures and longer exposure times than do stronger ions. The number of times that the contaminated fluid will flow through filter 30 is preselected and is programmed into controller 67. We have found that for most dissolved constituents one to ten thru puts is sufficient. Upon completion of the last desired flow thru or thru put of contaminated fluid through the filter, vacuum bleed valve 54 is closed by deenergizing its actuator and simultaneously reversible motor 34 is energized to release the clamping force applied to filter 30 by lifting container 13. In most cases the contaminated fluid will be an evaporative fluid, that is, one that will evaporate. In such cases, vacuum pump 28 and vacuum valve 52 will remain energized so that maximum vacuum is drawn into container 19 thereby drying the evaporative fluid from the filter 30 by drawing air through filter 30. Container 13 is raised by energization of reversible motor 34 causing drive sprocket 36 to be rotated in a clockwise direction thereby drawing chain 37 over sprocket 38 and lifting adapter link 42. By lifting adapter link 42 container 13 is caused to raise since L-clamp 48 is attached to container 13 by pin 49 and also fits over lever 46 thereby lifting container 13. At the end of the drying period vacuum valve 52 is de-energized thereby ceasing generation of any further vacuum in container 19. Filter 30 is then moved forward so that the portion containing the collected contaminants can be positioned over filter receptacle 64 and severed by cutter 63. The portion of the filter containing the contaminants is then inserted into the X-ray chamber 66 for analysis.

A vacuum line and valve is connected between vacuum pump 28 and filter receptacle 64 and also between pump 28 and X-ray chamber 66. These are not shown in the figures to avoid over-crowding the drawings. The vacuum in filter receptacle 64 holds the severed portion of filter 30 while receptacle 64 is swung over to chamber 66. Then the vacuum to chamber 66 is activated while the vacuum valve controlling the vacuum to receptacle 64 is de-activated. This causes the filter to be properly transferred to the X-ray chamber 66.

Container 13 is lifted a predetermined amount. As adapter link 42 is raised, it comes in contact with switch assembly 44 which de-energizes reversible motor 34 once container 13 is at the desired height.

Once the portion of filter 30 containing the collected contaminants is severed by cutter 63, filter 30 is withdrawn or retracted from between containers 13 and 19, and container 13 is brought back down on container 19 by the energization of reversible motor 34. Cleansing control valve 81 is then opened by energization of its associated solenoid 82 so that the flushing solution 72 in container 75 will flow through containers 11, 13, and 19. Exhaust outlet valve 24 is in a closed position and recirculating valve 22 is open while recirculating motor 57 is energized so that the flushing solution can be recirculated through pipes 58, 59 and containers 13 and 19. Recirculating pump 57 is then de-energized and exhaust valve 24 is actuated so that the flushing solution can drain through exhaust outlet or port 26.

Flushing solution 72 is stored in container 74 and is measured into container 75 when valve 78 is open by energization of its solenoid 79. As flushing solution 72 flows into container 75 float 76 actuates flow switch 77 when the proper level is obtained thereby closing valve 78 by de-energization of its solenoid 79.

Timer controller 67 controls the operation of the overall apparatus by interconnection with the various components via connectors 68, 69, 70, and 71.

In an apparatus of this type, the material comprising the surfaces that come in contact with the fluids being handled must be compatible with such fluids. Not only must they be impervious to damage by the fluids, they must have a negligible absorption affinity and must not react with the fluids in a manner to release particles into the fluid thereby giving a false indication of the contaminants within the fluid to be analyzed. The surfaces that come in contact with the fluids sould be of such materials as polyethylenes, polypropylenes, fluoropolymers, glass and where unavoidable, stainless steel such as AISI316. However, when glass is used precautions must be taken to prevent breakage.

Figure 2:
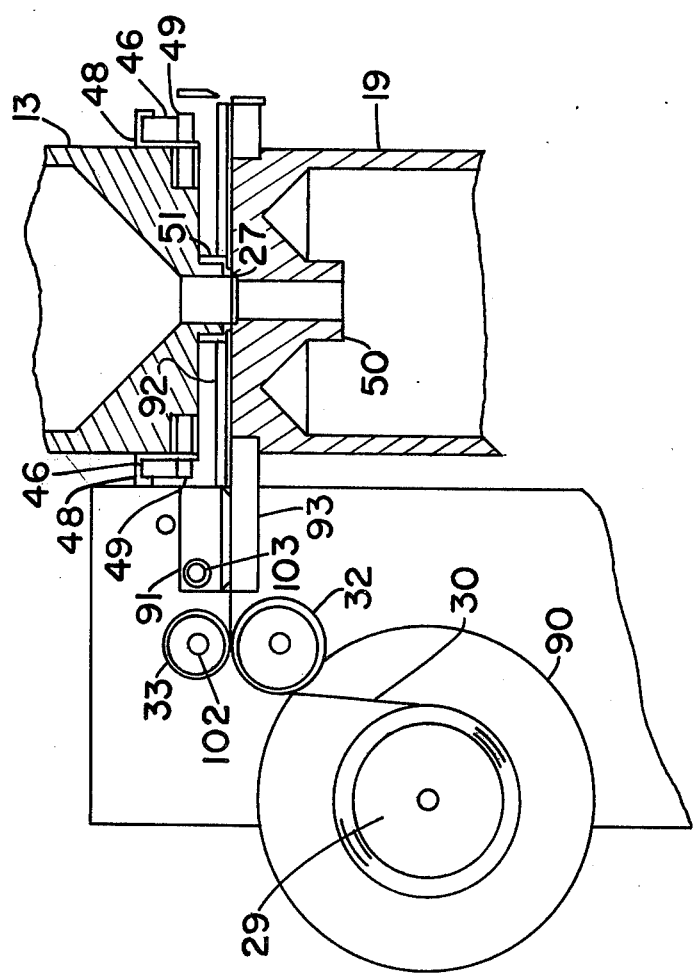
FIG. 2 is a sectional view with parts removed and parts broken away, showing a portion of the apparatus with trapping material and its path between two containers.

In FIG. 2 the path of contaminant trapping material or filter 30 can better be seen along with the clamped position of container 13 and container 19. Filter 30 is wound on supply spool 29 which has flanges, one of which is removed for illustration purposes. Flanges 90 overlap the ends of drive roller 32 so that spool 29 remains in alignment with driver roller 32. Idler roller 33 presses down on filter 30 to maintain filter 30 in contact with driver roller 32 so that filter 30 is pushed by driver roller 32 between pressure block 91 and support block 93 and into filter guide 92. Filter guide 92 is formed by a channel with undercut grooves along its sides. The edges of filter 30 engage these grooves which guide the leading edge corners, suppressing them and preventing filter 30 from becoming jammed while it is being advanced.

In FIG. 2 we can see that there are actually two levers 46 and each one rests on a pin 49 which is embedded in container 13. Each lever 46 is also held in position over pin 49 by an L-shaped clamp 48 which clamp also fits onto pin 49. Filter 30 must be accurately positioned so that it fits between sealing ring 51 of container 13 and inlet 50 of container 19. Otherwise, all of the fluid passing through the containers will not pass through filter 30. Sealing ring 51 is made from a structural plastic material such as acetal plastic and receives the clamping force exerted on container 13. In most cases container 13 will be made of a material that will deform under the clamping force, therefore ring 51 is provided. Sealing ring 51 is not a gasket but holds filter 30 firm enough so that filter 30 serves as its own gasket, no other gasket is used. The force of ring 51 and the vacuum in container 19 prevent any wicking of fluid from occurring in the filter material on the outside of ring 51.

Porous disk 27 is mounted flush with the top of container 19 and supports filter 30 so that fluid flow 30 so that fluid flow through the filter does not rupture the filter. Note how inlet 50 is recessed into container 19. This arrangement permits the vacuum pump outlet to be located near the top of container 19 and not withdraw any of the fluid that will pass into container 19 through inlet 50 while the vacuum pump is evacuating container 19.

Figure 3:
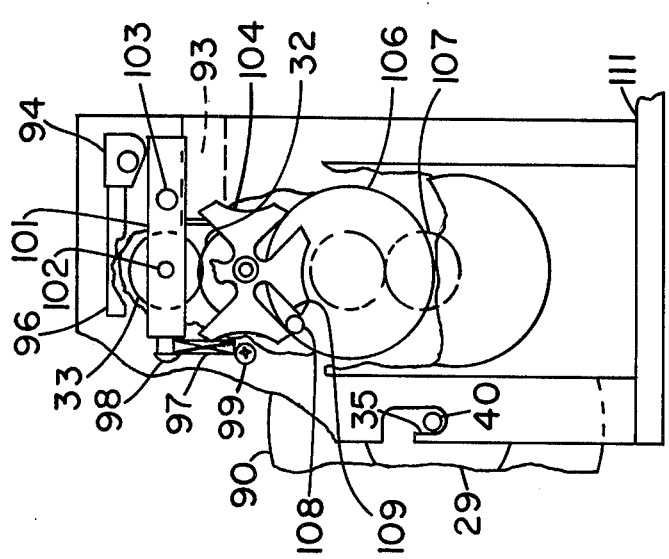
FIG. 3 is a view, with parts removed and parts cut away, of the mechanism used to feed the contaminant trapping material.

FIG. 3 better illustrates a Geneva mechanism arrangement used to advance filter 30. Filter supply spool 29 is free to rotate about shaft 40. Shaft 40 is held in J slots 35. Supply spool 29 has flanges 90 which overlap drive roller 32. Gear 107 is attached to reversible drive motor 31 (illustrated in FIG. 1) which in turn drives another gear which mates with shaft of Geneva drive wheel 106. Drive wheel 106 has a peg 108 extending from its face and fitting into a slot 109 which is one of four slots that are contained by a four point Geneva star wheel 104. Peg 108 causes the Geneva star wheel to rotate one quarter turn every time that it is engaged in a slot 109 as drive wheel 106 rotates. This arrangement allows the tape to be advanced a precise amount upon command, and by driving gear 107 with a reversible motor the tape can be moved forward or backward a precise amount.

To facilitate starting the filter tape 30 a lever arm 96 is provided which is attached to a cam 94. When lever arm 96 is raised, cam 94 places a pressure on idler support 101 which in turn pivots about pin 103 causing idler roller 33 to raise since it is mounted on shaft 102 which is held in idler support 101 and, as illustrated in FIG. 2, pressure block 91 is loosely held by pin 103. When lever arm 96 is released, spring 97 will pull idler support 101 down thereby bringing idler roller 33 back into contact with power drive roller 32. Spring 97 is held to one end of idler support 101 by a screw 98 while the other end of spring 97 is fixed to the frame by screw 99. The frame is mounted on base 111.

Figure 4:
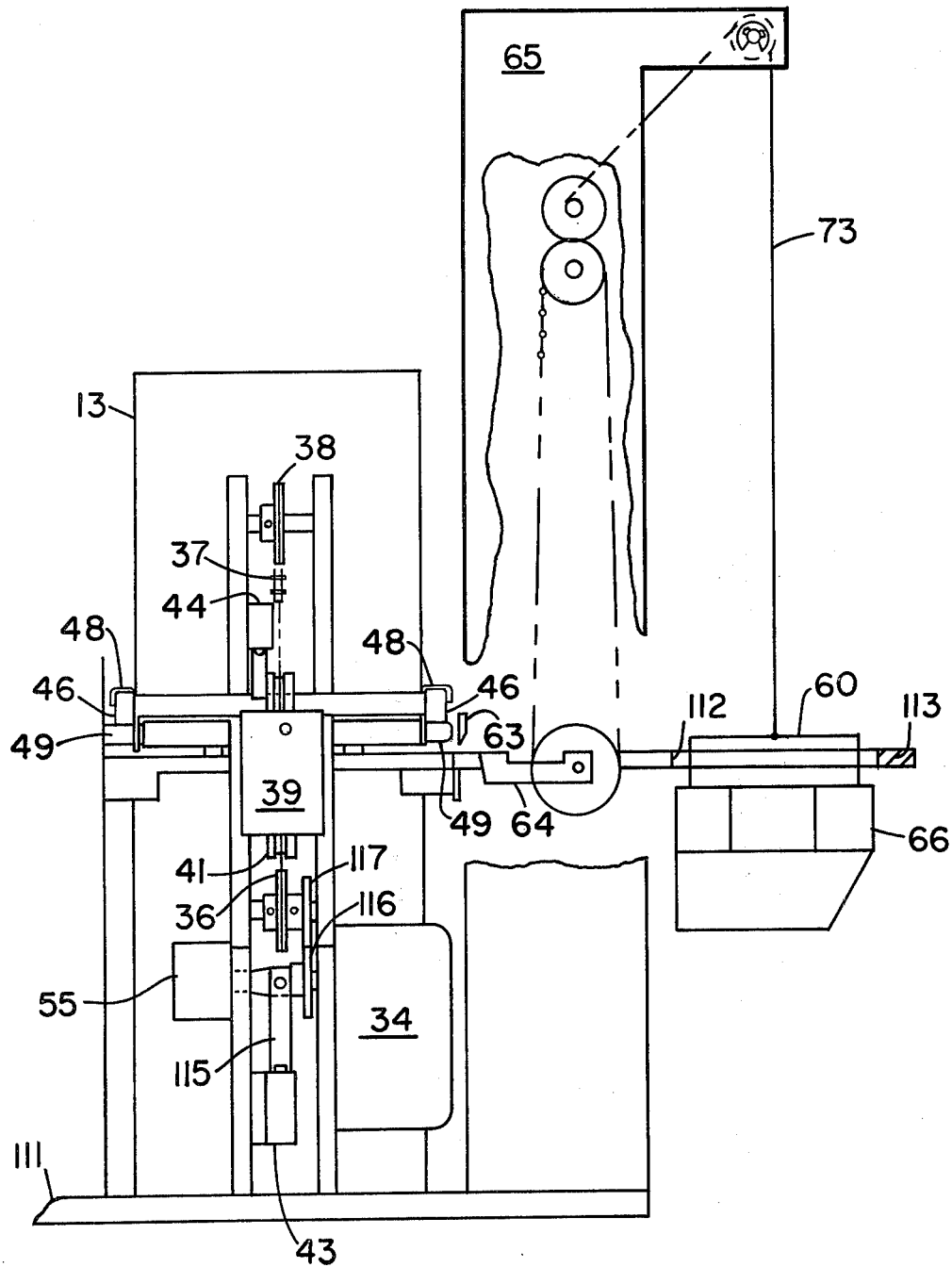
FIG. 4 is a side view of a portion of the apparatus with parts cut away.

FIG. 4 shows a continuation of base 111 from FIG. 3 and the equipment mounted thereon. Reversible motor 34 has drive gear 116 and switch actuator 115 mounted on its shaft. Switch actuator 115 actuates switch assembly 43 when container 13 has been drawn down the proper amount to securely hold the filter material 30 between container 13 and container 19. Actuation of switch assembly 43 removes power from reversible motor 34 and applies power to electromagnetic brake 55. Electromagnetic brake 55 is provided to insure that once power is removed from reversible motor 34, the clamping force on filter material 30 is maintained. Actuator 115 is adjustable on the shaft of reversible motor 34 and is an alternate way of actuating switch assembly 43 from that illustrated in FIG. 1. Driven gear 116 mates with gear 117 which together form a one to one gear ratio. The operation of the draw mechanism is explained in greater detail hereinafter.

When filter cutter 63 severs the portion of the filter having the sample of contaminants, filter receptacle or transporter 64 carries the filter over to X-ray chamber 66 so that X-ray analysis may be performed on the contaminants trapped by the filter. X-ray chamber shield 60 is lifted by cable 73 while transporter 64 is carrying the filter sample so that transporter 64 can move through opening 112 in support frame 113 to deposit the filter sample on X-ray chamber 66. Presentation subassembly 65, as illustrated, is intended for use with a particular X-ray analysis apparatus and serves the purpose of presenting the portion of filter on which the contaminants are collected for analysis. Other presentation systems are required for X-ray analysis apparatus of different designs. For example, in many X-ray machines the X-ray chamber is mounted above the sample to be analyzed, and in such cases the sample would simply be advanced until it appears under the X-ray chamber. Use of an above mounted X-ray chamber would in most cases result in a less complex presentation subassembly 65.

Presently there are two major methods of X-ray spectrometry for analysis of ion exchange or chelating resin loaded filter material containing heavy metal ions. These methods are energy dispersive X-ray analysis and wavelength dispersion X-ray analysis. The basic difference between the two methods is in the detection system used in the instruments. However, the main advantage of the energy dispersive method is the simultaneous multi-element capability. It should be noted that energy dispersive X-ray analysis is the same as non-dispersive X-ray analysis.

Figure 5:
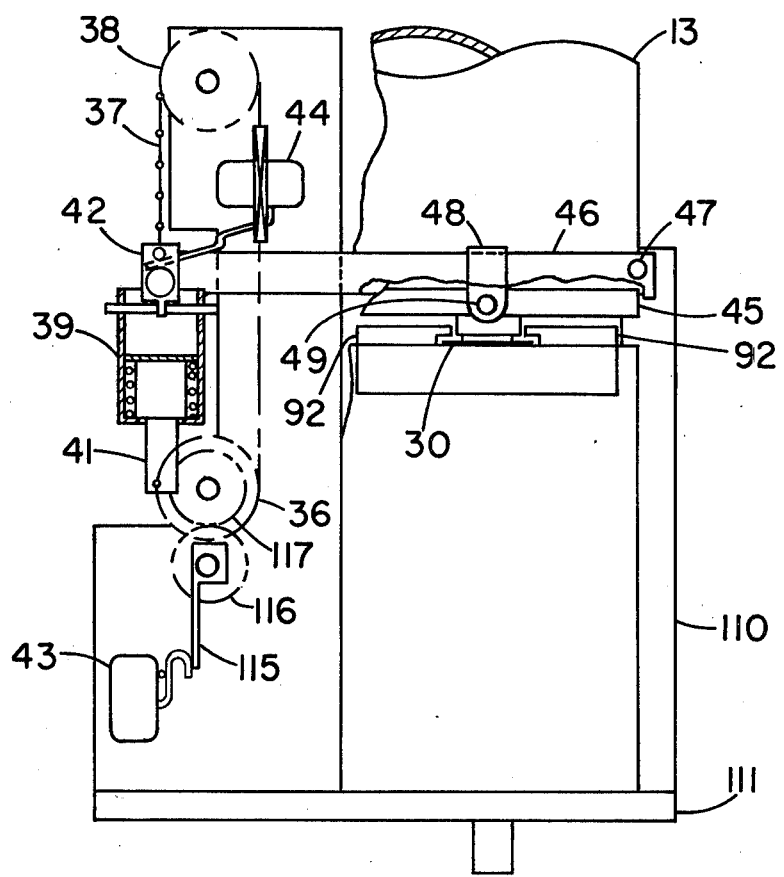
FIG. 5 is a side elevation, with parts removed and parts broken away, of a portion of the apparatus showing the mechanism used to clamp two of the containers together.

In FIG. 5 the operative of the draw mechanism to draw container 13 down to container 19 is illustrated. Lever 46 is pivoted about pin 47 supported by frame 110 which is attached to base 111. Drive gear 116 drives gear 117 which causes drive sprocket 36 to rotate thereby moving chain 37 around sprocket 38. Lever 46 rests on pin 49 which is embedded in a structural ring 45 which surrounds the bottom of container 13. L-shaped clamp 48 fits over the top of lever 46 and is also fixed to pin 49. Therefore, as draw bar link 42 is moved up and down by chain 37 lever 46 causes container 13 to move up and down. As container 13 is moved downwardly it fixedly holds contaminant trapping material 30 in place with sufficient force to prevent leakage and avoid wicking. The contaminant trapping material is guided between containers 13 and 19 by channels 92. Preferably the contaminant trapping material is supported on a porous screen such as porous polyethylene to prevent the contaminant trapping material from being ruptured by the fluid flowing through it (see disk 27 in FIG. 2).

Figure 6:
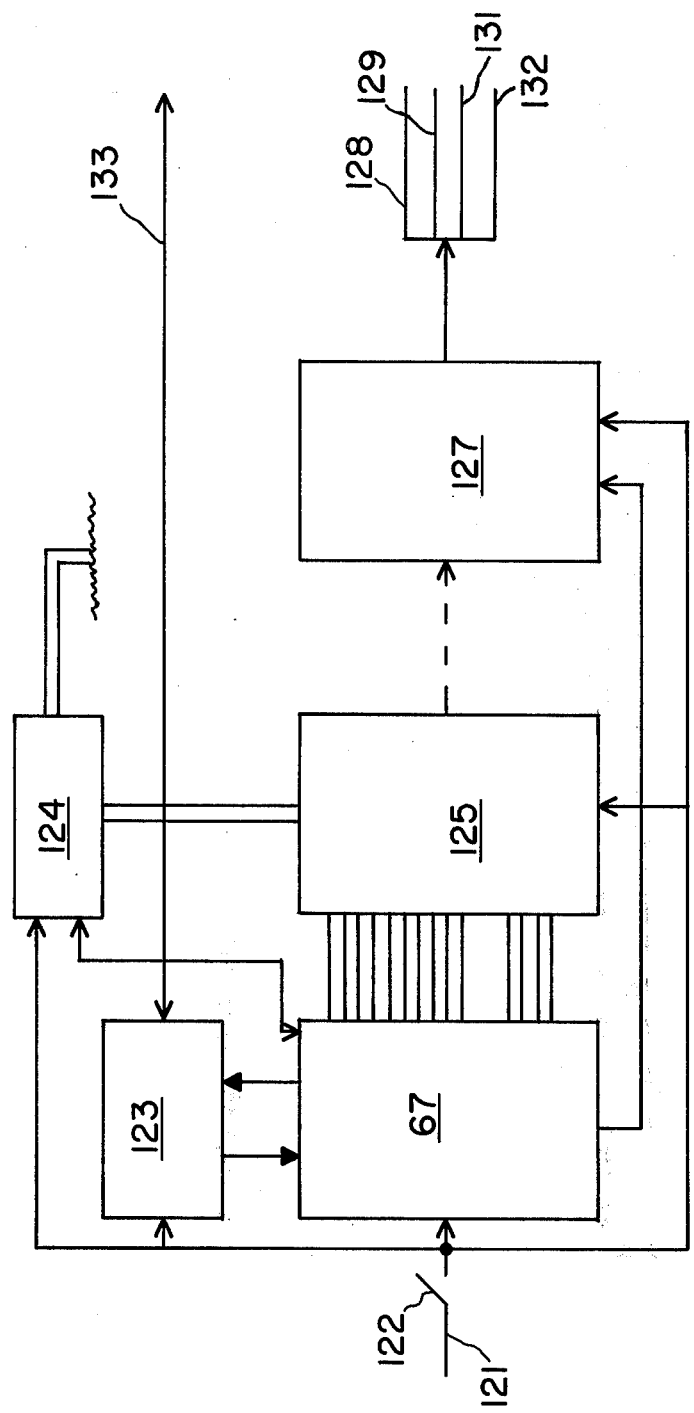
FIG. 6 is an overall schematic block diagram of the system.

FIG. 6 is an overall block diagram of the apparatus. Power input is on line 121 and is applied when switch 122 is closed. Timer or controller 67 controls the sequence of functions while programmer 123 provides the necessary inputs to controller 67, such as the number of thru puts. Source 124 supplies the contaminated fluid to be analyzed into the system 125. System 125 is better illustrated in FIGS. 1 through 5. Once the sample has been collected, it is analyzed by analyzer 127. FIG. 6 illustrates how the overall apparatus can be remotely controlled. Remote control line 133 is connected to programmer 123 and can provide an initiating command. Once a sample has been analyzed by an analyzer 127, the results can be transmitted to a remote location by teletype line 128, HF/UHF transmission line 129, telephone line 131, or satellite data link 132. It should therefore be appreciated that not only has a new and novel sample collection and presentation apparatus been provided, but also one that is automatic and easily adaptable to remote use and operation.

Figure 7:
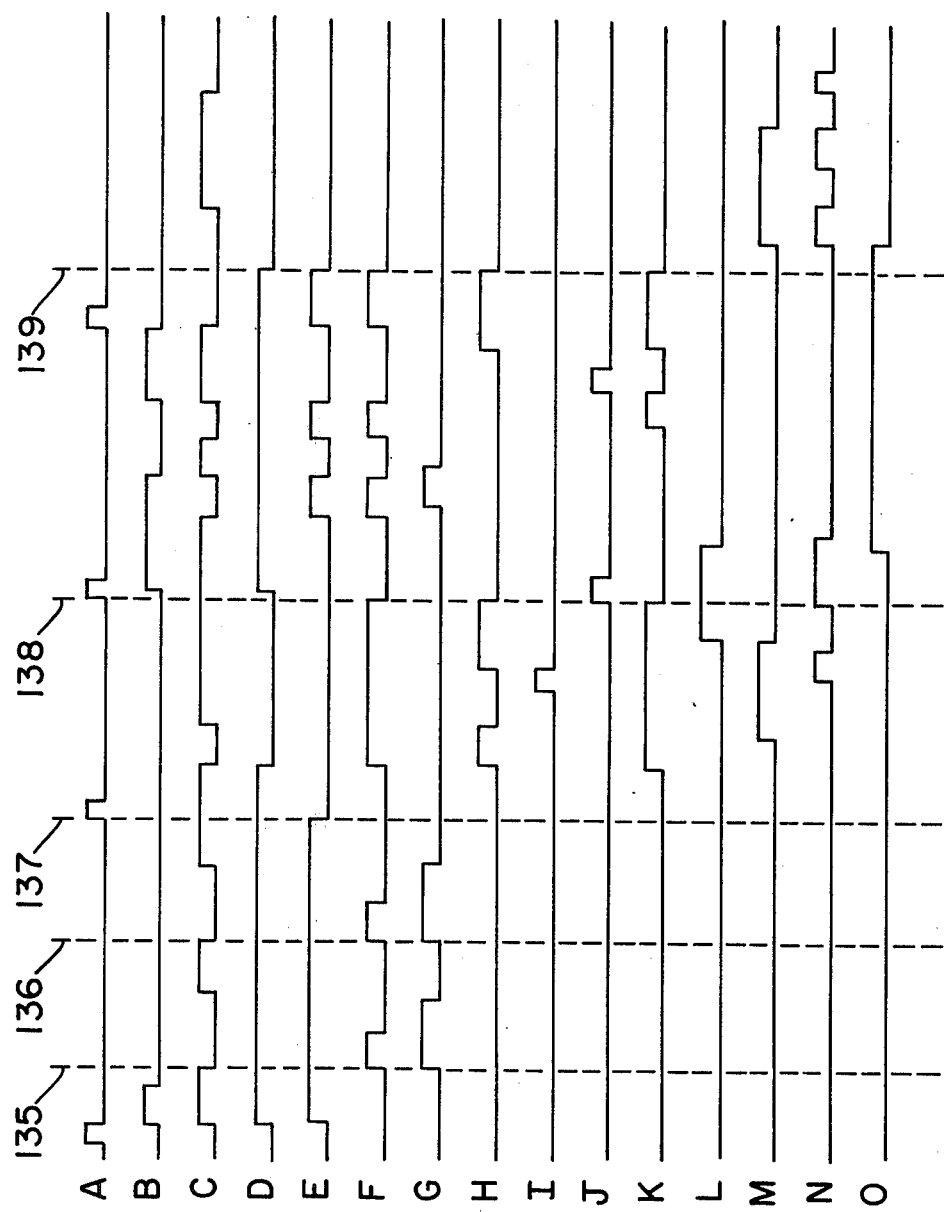
FIG. 7 is a timing chart that shows a timing relationship of the different functions of the apparatus of FIG. 1 when it is fully automated.

The timing and synchronization for the overall system is shown in FIG. 7. Pulse A starts reversible motor 34 (see FIG. 1) to bring containers or tanks 13 and 19 together. Pulse B controls valve 17 and allows the premeasured fluid to enter container or tank 13. Pulse C starts vacuum pump 28. Pulse D opens valve 52 and allows tank 19 to be vacuumized. Pulse E opens valve 54 so that preset valve 53 can regulate the amount of vacuum in tank or container 19. Pulse F opens valve 22 so that the fluid in container 19 can be recirculated. Pulse G actuates recirculating pump 57. Pulse H controls reversible motor 31 so that the contaminant trapping material can be advanced or retracted. Pulse I controls cutter 63 so that the portion of the filter material containing the sample can be severed for presentation. Pulse J controls valve actuator 82 and allows the system to be purged or flushed. Pulse K controls valve 24 that permits the system to be drained.

Pulses L, M, N, and O all relate to the presentation subassembly illustrated which can be used with an X-ray chamber that accepts a sample to be analyzed at the top of the chamber. Pulse L controls a vacuum valve that feeds the X-ray chamber 66. Pulse M controls a vacuum valve that supplies vacuum to the filter receptacle or transporter 64. Pulse N controls a reversible motor (not shown) that powers transporter 64 and its associated cables and pulleys. Pulse O controls the X-ray machine that analyzes the sample.

The pulses of FIG. 7 represent the timing portion output of controller 67 and normally actuate relays or electronic switches within the controller. A schematic for the controller is not shown, because it will be readily apparent to those skilled in the art as to the necessary logic circuitry required to obtain the illustrated pulses. The circuitry required could be discrete components, logic chips, or hybrid components.

Dotted line 135 indicates the beginning of a recirculation thru put. Recirculating valve 22 is opened by pulse F and recirculating motor 57 is energized by pulse G. Dotted line 136 is the commencement of a second recirculating thru put and dotted line 137 is the completion of the thru put and commencement of a drying of the collected sample by separating tanks 13 and 19 with pulse A and allowing the vacuum generator to draw air over the sample. A flush cycle begins with dotted line 138 and during the flush cycle X-ray analysis begins. Arriving at dotted line 139 a new portion of contaminant trapping material is in place and then begins the return of the filter transporter 64. Vacuum is reapplied to transporter 64 so that the analyzed sample can be lifted from the X-ray chamber and discarded prior to the transporter returning to its ready position. At the completion of the cycle commencing at dotted line 139, the system is ready to receive another start command on line 133 of FIG. 6 so that another sample can be analyzed.

By now it should be apparent that we have provided a novel automatic system to collect and analyze contaminants from a sample of fluid. The automatic system can pass the fluid to be sampled through a contaminant trapping material any number of times required to properly sample the fluid and can analyze the collected contaminants by the use of X-ray analysis.

Consequently, while in accordance with the Patent Statutes, we have described what at present are considered to be the preferred forms of our invention it will be obvious to those skilled in the art that numerous changes and modifications will be made herein without departing from the true spirit and scope of the invention, and it is therefore aimed in the following claims to cover all such modifications.

What we claim as new and desire to secure by Letters Patent of the United States is:

1. An apparatus to collect and concentrate dissolved constituents from a known volume of fluid, comprising: a first container to receive the known volume of fluid and having an outlet; an ion exchange material positioned at the outlet of the first container so that all the fluid leaving the first container passes through the ion exchange material; a second container to receive the fluid from the first container; reversible means to move the first container and the second container together thereby fixedly holding the ion exchange material in place; a vacuum generating means to create a vacuum in the second container, the second container having an inlet extending into the interior so that a vacuum outlet located near the wall having the inlet does not withdraw the fluid being sampled; means to recirculate the fluid from the second container back to the first container to allow the fluid to pass through the ion exchange material again to extract additional dissolved constituents; a sensor detects disappearance of fluid in the first container and in turn disables the vacuum generating means; and means to introduce deionized water into the measuring container after contaminated fluid has been drained from the apparatus, the deionized water being provided to flush the containers and the means to recirculate.

2. An apparatus to collect and concentrate contaminants from a known volume of fluid, comprising: a sample measuring container having a controllable outlet; a receiving container to receive the contents from the measuring container and having an outlet; a contaminant trapping material positioned on the outside of the receiving container at the outlet; an accumulating container which accumulates the fluid from the receiving container; at least one pivoted lever to bring the receiving container and the accumulating container together to fixedly hold the contaminant trapping material therebetween; recirculating means to pass the fluid from the accumulating container back to the receiving container so that the fluid can pass through the contaminant trapping material more than once; vacuum generating means to create a vacuum in the accumulating container when the accumulating container and receiving container are fixedly holding the contaminant trapping material; and flushing means to flush the containers and the recirculating means after the fluid has been sampled, the accumulating container having an outlet to allow the fluid to be recirculated or to be exhausted from the apparatus once the fluid has been passed through the contaminant trapping material a predetermined number of times.

3. A method of collecting and concentrating contaminants from a known volume of fluid, comprising: measuring a sample of fluid; placing a contaminant trapping material between a first and a second container; bringing the first and second containers together; emptying the sample of fluid into the first container; generating a vacuum in the second container to assist the flow of fluid from the first container to the second container through the contaminant trapping material; recirculating the sample of fluid from the second container back to the first container through a recirculating path so that the sample of fluid will pass through the contaminant trapping material again; draining the sample of fluid from the containers; separating the first and second containers; advancing the contaminant trapping material; presenting the material for analysis; bringing the first and second containers back together without the contaminant trapping material between them; and flushing all the containers and the recirculating path to remove any contaminants that may not have drained.

4. An apparatus to collect contaminants from a fluid comprising:
 a sample tank to premeasure the fluid to be analyzed;
 a receiving tank to receive the premeasured sample having an outlet at its lowest portion;
 a continuous roll of contaminant trapping material;

an accumulating tank to accumulate the fluid from the receiving tank and having an inlet; a portion of the contaminant trapping material being positioned between the receiving tank and the accumulating tank so that all the fluid passes through the portion of contaminant trapping material as the fluid passes from the receiving tank to the accumulating tank;

a vacuum generating means to create a vacuum in the accumulating tank and having an evacuating port near the inlet of the accumulating tank;

means to recirculate the fluid from the accumulating tank to the receiving tank so that the fluid can be passed through the portion of contaminant trapping material repeatedly to further trap contaminants;

a container of non-contaminated fluid controllably connected to the sample tank, the non-contaminated fluid being provided to flush the apparatus thereby removing traces of any contaminated fluid remaining in the apparatus; and reversible drive motor means for exercising a Geneva mechanism so that the contaminant trapping material is removed from the flow of non-contaminated fluid during flushing of the apparatus.

* * * * *